United States Patent [19]

Wong

[11] Patent Number: 4,730,112

[45] Date of Patent: Mar. 8, 1988

[54] OXYGEN MEASUREMENT USING VISIBLE RADIATION

[75] Inventor: Jacob Y. Wong, Santa Barbara, Calif.

[73] Assignee: Hibshman Corporation, San Luis Obispo, Calif.

[21] Appl. No.: 863,315

[22] Filed: May 15, 1986

Related U.S. Application Data

[63] Continuation-in-part of Ser. No. 837,605, Mar. 7, 1986, abandoned.

[51] Int. Cl.[4] .................................. G01N 21/61
[52] U.S. Cl. .................................. 250/343; 250/341
[58] Field of Search ............... 250/343, 340, 341, 339, 250/373; 356/39, 40, 41; 128/633, 634; 372/20, 43

[56] References Cited

U.S. PATENT DOCUMENTS 4,192,996  3/1980  Kronick et al. ................. 250/373

OTHER PUBLICATIONS

Norton et al, ". . . Wavelength Tuning . . . of Lasers", Applied Phys. Let., vol. 18, #4, (Feb.–71), p. 158.
Clark et al, ". . . Wavelength Tuning . . . of GaAlAs . . . ", IEEE Jour. of Quant. Elect., vol. QE-18, #2 (1982), p. 199.
Vaucher et al, ". . . Tunable Pulses from . . . Laser", IEEE Jour. of Quant. Elect., vol. Q-E, #2 (1982), p. 187.
Anzin et al, "Freq. Tuning . . . by Pressures & Temp.", Sov. J. Quant. Elect., vol. 7, #6 (1977), p. 793.

Primary Examiner—Janice A. Howell
Assistant Examiner—Richard Hanig
Attorney, Agent, or Firm—Daniel C. McKown

[57] ABSTRACT

Apparatus for measuring the absorption of a gaseous sample and particularly suitable for measuring the concentration of gaseous oxygen makes use of a diode laser whose emission wavelength is adjacent to but spaced from the wavelength of a distinct absorption line. The diode drive current is altered to cause the junction temperature of the laser to change, thereby changing the wavelength of the emitted radiation and in effect scanning it through a range of wavelengths that includes the absorption line. The absorption is determined by a ratio technique and therefore is independent of changes in the laser output power level and drifts and changes in other parts of the optical system.

8 Claims, 14 Drawing Figures

OXYGEN MEASUREMENT USING VISIBLE RADIATION

BACKGROUND OF THE INVENTION

Reference to Copending Application

The present application is a continuation-inpart of U.S. patent application Ser. No. 837,605 filed on Mar. 7, 1986 now abandoned for OXYGEN MEASUREMENT USING VISIBLE RADIATION.

Field of the Invention

The present invention is in the field of gas analysis and more specifically relates to apparatus for measuring the concentration of gaseous oxygen present in a volume by measuring the absorption of visible radiation passing through the gaseous sample.

The Prior Art

The present application is concerned with an entirely new way of measuring the concentration of gaseous oxygen, and is particularly suitable for use in compact instruments such as might be used in medical applications. As will be described below, previously known ways of measuring oxygen concentration have suffered from poor accuracy, slow response time, and interference by other gases. With the exceptions of mass spectrometry and gas chromotography, the various methods of measuring gaseous oxygen can be classed into three main groups: paramagnetic, thermoconductive, and electrochemical. These techniques will now be briefly described.

The paramagnetic technique makes use of the paramagnetism of oxygen. The permeability of oxygen at a pressure of 1 atmosphere and at 20 degrees centigrade is 1.00000179. In the so-called Pauling method, the gas is introduced into a cell in which a small dumbbell is suspended on a taut platinum ribbon. The cell is held in a nonuniform magnetic field. The torque on the dumbbell is proportional to the volume magnetic susceptibility of the gas around the dumbbell. This torque is counteracted by the electromagnetic effect of a current which is made to flow through a single turn of platinum wire wound on the dumbbell. The current required to do this is proportional to the original torque and is therefore a measure of the susceptibility of the sample gas. This restoring current is maintained at the correct value automatically by means of a twin photocell which detects the position of a beam of light reflected from a mirror on the suspended dumbbell. The electrical outputs are derived from the restoring current.

There are several drawbacks to this Pauling method. First, its response is slow (typically 10 seconds for 90 percent of full scale). Second, it is nonspecific in the sense that significant interferences are caused by other paramagnetic gases, namely NO and $NO_2$. Third, since the position of the dumbbell at rest determines the readout and any gas flow blows the dumbbell away from the correct position, this method is not suitable for the measurement of flowing oxygen gas.

The thermoconductivity method is based on the rate at which different gases remove heat from a hot wire. Oxygen conducts heat at a different rate than nitrogen. The rate at which a temperature-sensitive thermistor is cooled in the sample chamber therefore deoends on the oxygen concentration in the chamber. The rate of cooling of this thermistor is compared with that of a similar thermistor in a reference chamber by means of a Wheatstone bridge. The difference is displayed as a meter reading of the oxygen concentration. Silica gel is utilized to equalize the content of water vapor in both the sample and reference chambers so that the readings are not affected by the water vapor.

The thermoconductivity method suffers from a rather slow response (typically 10 seconds from 0 to 90 percent of full scale reading) and cannot be used for monitoring flowing oxygen due to the fact that the rate of cooling depends on the flow rate. Like the Pauling paramagnetic technique, the thermoconductivity method permits only intermittent analysis due to the need for manually introducing the gas into the sampling chamber.

All of the commercially-available continuous oxygen monitors operate on the electrochemical principle. There are two basic types of these instruments: the polarographic and the galvanic. Both of these have porous metal sensing electrodes (anode and cathode) with a gas-tight conducting electrolyte between them. The gas-tight electrolyte prevents mixing of gases between the anode chamber and the cathode chamber of the cell, but allows electrochemical oxygen transfer between anode and cathode. Transport of electrochemical oxygen (either in the form of cations or oxide ions) between the cathode and anode chambers (one of which is at a fixed oxygen partial pressure for reference) generates an electrical signal which is directly proportional to the partial pressure of oxygen in the sample chamber. Since the diffusion of electrochemical oxygen through the electrolyte depends on temperature, a thermistor is used to regulate the current so that the only variable measured is oxygen concentration in the sample chamber. The difference between the polarographic and the galvanic operation is that the former requires a polarizing voltage from an external power supply for the oxygen transport, whether as the latter acts as a fuel cell and derives its polarizing voltage internally. Oxygen monitors operating on the electrochemical principle are usually slow, although response times of 100 milliseconds have been obtained with the use of very high temperature electrolyte for speeding up the transport of electrochemical oxygen. The adaptation of electrochemical techniques to flowing oxygen measurement is difficult because of the inevitable masking of the sample electrode by the condensations of water vapor such as might be present in a medical application.

In addition to the three main methods discussed above, the possibility of measuring the gaseous oxygen concentration through ultraviolet absorption has been explored by the present inventor in U.S. Pat. No. 4,096,388, and by Kronick, et al. in U.S. Pat. No. 4,192,996. The major problem with the ultraviolet absorption technique is interference by other gases which also absorb ultraviolet radiation in the same portion of the spectrum.

Thus, methods of measuring the concentration of oxygen in a gaseous sample have suffered from a number of deficiencies which have limited the practical usefulness of the techniques, particularly in medical applications.

SUMMARY OF THE INVENTION

There is no known strong absorption band for $O_2$ in the visible and near infrared. However, the existence of three very weak absorption bands of $O_2$ located at 760 nm, 1.07 $\mu$m and 1.27 $\mu$m respectively has been known since the early 1960's. The 760 nm band, also called the "A" system, lies at the very edge of the red end of the visible spectrum and arises from the electronic-rotational $X^3\Sigma_g^- \rightarrow b'\Sigma_g^+$ transition of the oxygen molecule. This is a spin-flip transition involving the spin change of a $\pi_g^-$ electron. The weakness of this system indicates that it is a magnetic dipole transition. The O—O band of the "A" system of oxygen spans approximately from 759 nm to 773 nm and comprises 72 sharp lines making up four distinct branches designated as $P_P$, $P_Q$, $R_R$ and $R_Q$ respectively (see FIG. 1). The equivalent widths of the strongest of these sharp lines ranges between 0.1 and 0.15 nm.

The infrared atmospheric oxygen bands at 1.07 μm and 1.27 μm, represent a magnetic dipole $'\Delta_g \rightarrow ^3\Sigma_g^-$ transition and comprises eight distinct branches (P, R, $Q_P$, $S_R$, $Q_R$, $P_Q$, $R_Q$ and $Q_Q$) The absorption strengths of these bands are even less than those observed for the "A" system.

The implementation of an oxygen monitor using the aforementioned visible and infrared atmospheric oxygen bands in an absorption technique has heretofore been considered unfeasible because of the extraordinary weakness of these bands and the lack of adequate source, detector, sample chamber and methodology.

The present invention consists of apparatus that permits the monitoring of $O_2$ concentration using a novel optical absorption technique operating in the 760 nm O—O band of the oxygen "A" system.

The present invention is made feasible by the relatively recent advent of semiconductor laser diode light sources such as the AlGaAs system with emission wavelengths spanning the O—O band of the oxygen "A" system, the availability of the silicon photodiode detector which has optimum response in the 760 nm region, the use of a special sample chamber design that permits long path lengths to be obtained in a relatively compact space and the application of a novel spectral scanning technique.

Due to the extreme weakness of the oxygen "A" system at 760 nm (the intensity modulation for a 2.5 nm band pass filter and a path length of three meters has been deduced from experimental measurements as being on the order of $1.67 \times 10^{-5}$ per atmosphere per cm) the use of a relatively broadband source (>10 nm) such as an incandescent lamp or an LED with a narrow bandpass filter to cover all the sharp lines of the O—O band of the oxygen "A" system does not yield sufficient intensity modulation to render feasible an absorption technique for the detection of this gas.

Instead a much narrower spectral source such as a single mode or a multi-mode laser whose emission line widths match closely to those of the oxygen sharp lines and cover only one or at most several of the strongest absorption lines of the O—O band is necessary in order to provide the minimum needed modulation.

The use of a reflecting integrating sphere as a novel sample chamber for providing a long and adjustable path length ensures the fact that sufficient modulation is available if required.

The use of novel optical and thermal feedbacks working in conjunction with the laser diode provides a stable spectral output, which is needed for the absorption scheme.

Finally, a novel laser current drive scheme is used to achieve a thermally-driven spectral scanning of the laser output in and out of the oxygen absorption lines to provide the "reference" and "sample" conditions for the measurement of oxygen in the sample chamber.

The novel features which are believed to be characteristic of the invention, both as to organization and method of operation, together with further objects and advantages thereof, will be better understood from the following description considered in connection with the accompanying drawings in which a preferred embodiment of the invention is illustrated by way of example. It is to be expressly understood, however, that the drawings are for the purpose of illustration and description only and are not intended as a definition of the limits of the invention.

DETAILED DESCRIPTION OF THE PREFERRED EMBODIMENT

Figure 1:
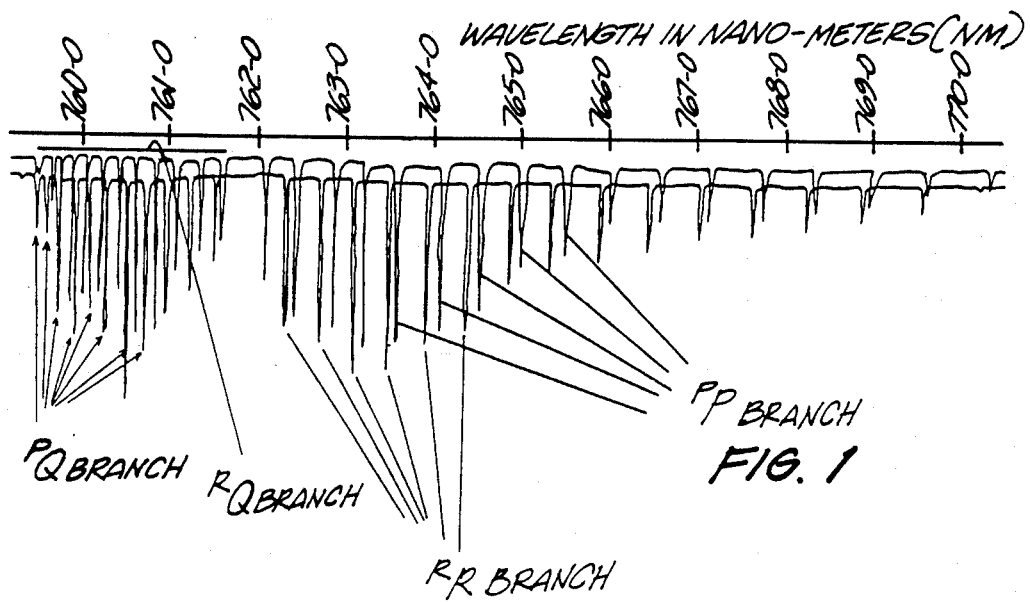
FIG. 1 is a graph showing the various absorption lines that comprise the oxygen "A" system as a function of wavelength.

FIG. 1 shows the absorption spectrum for the 760 nm O—O band of the oxygen "A" system showing the four distinct branches comprising a total of approximately 72 sharp lines. The vertical scale is greatly magnified to show the band. The intensity modulation for this band deduced from experimental measurements using a 2.5 nm bandpass filter and a three meters path length is on the order of $1.67 \times 10^{-5}$ per atmosphere per cm. This is extremely weak and has generally been considered to be impractical for use in the measurement of gaseous oxygen using a standard optical absorption technique. In the present invention this extraordinarily low modulation factor is circumvented by the use of a narrow spectral source that matches the linewidth of the strongest of the sharp lines in a novel spectral scanning mode, and also by the use of a novel sample chamber that provides a long path length.

Figure 2:
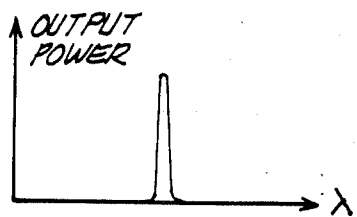
FIG. 2 is a diagram showing the output power of a single mode diode laser as a function of wavelength.
Figure 3:
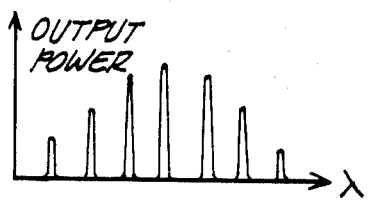
FIG. 3 is a diagram showing the output spectrum of a multi-mode diode laser versus wavelength.

Stable continuous wave (cw) semiconductor diode lasers fabricated out of the AlGaAs ternary alloy system whose spectral outputs span the 750-870 nm region with powers on the order of milliwatts (mw) have recently become available. These diode lasers can be fabricated using an index-guided structure to yield the so-called single mode output with all the power concentrated in just one very narrow spectral line as depicted in FIG. 2. Alternatively, they can be fabricated using a gain-guided structure to yield the so-called multi-mode output with a number of evenly spaced narrow spectral lines as depicted in FIG. 3. The spectral spacing between the emission lines is dependent upon the laser structural design. The spectral linewidth of individual emission lines for both the single and multi-mode diode lasers typically ranges from 0.01 to 0.9 nm and is of the same order of magnitude as that for the absorotion lines of the 760 nm O—O band of the oxygen "A" system.

This close matching of the linewidths between the diode laser emission lines and the oxygen absorption lines greatly increases the modulation factor. For the single mode diode laser the emission line is made to coincide under normal operating conditions with one of the strongest sharp lines of the oxygen "A" O—O band. For the multi-mode diode laser the spacing between the multiple emission lines is designed to match a contiguous set of oxygen absorption lines under normal operating conditions.

It is well known that the spectral output of diode lasers (both single- and multi-mode) shifts to longer wavelength as a function of increasing laser diode junction temperature. Concomitantly, the output power decreases if the drive current is held constant. For the AlGaAs semiconductor diode laser system the temperature coefficient of wavelength is slight, is approximately 0.3 nm/° C. The decrease in output power as a function of junction temperature increase, on the other hand, depends on a number of parameters including the laser structural design and its material composition.

The present invention makes use of the dependence of laser wavelength on the temperature of the laser diode junction. In accordance with the present invention, the wavelength of the diode laser is scanned through a range of wavelengths by varying the current through the diode. Clearly, this affects the power output of the diode laser, and it is found that the radiant output of the laser increases, on balance, when the current is increased.

Figure 4:
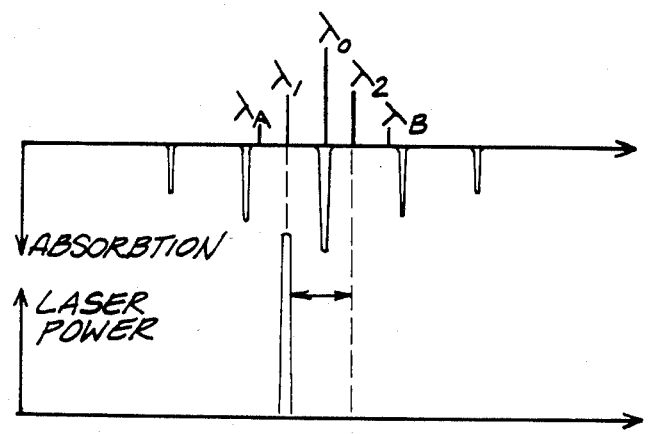
FIG. 4 is a diagram showing a diode laser output spectrum superimposed on an absorption spectrum as a function of wavelength.

FIG. 4 is a diagram showing the output of a single mode diode laser superimposed on a group of several absorption lines. In accordance with the present invention, a wavelength interval from $\lambda_A$ to $\lambda_B$ is found which interval contains only a single well-defined absorption line. In accordance with the present invention, the laser wavelength is scanned through the interval $\lambda_1$ to $\lambda_2$ which is entirely contained within the interval $\lambda_A$ to $\lambda_B$, and which includes the wavelength $\lambda_0$ of the absorption line. In the preferred embodiment of the invention, the scanning of the laser output wavelength is achieved by varying the current through the laser diode.

Figure 5:
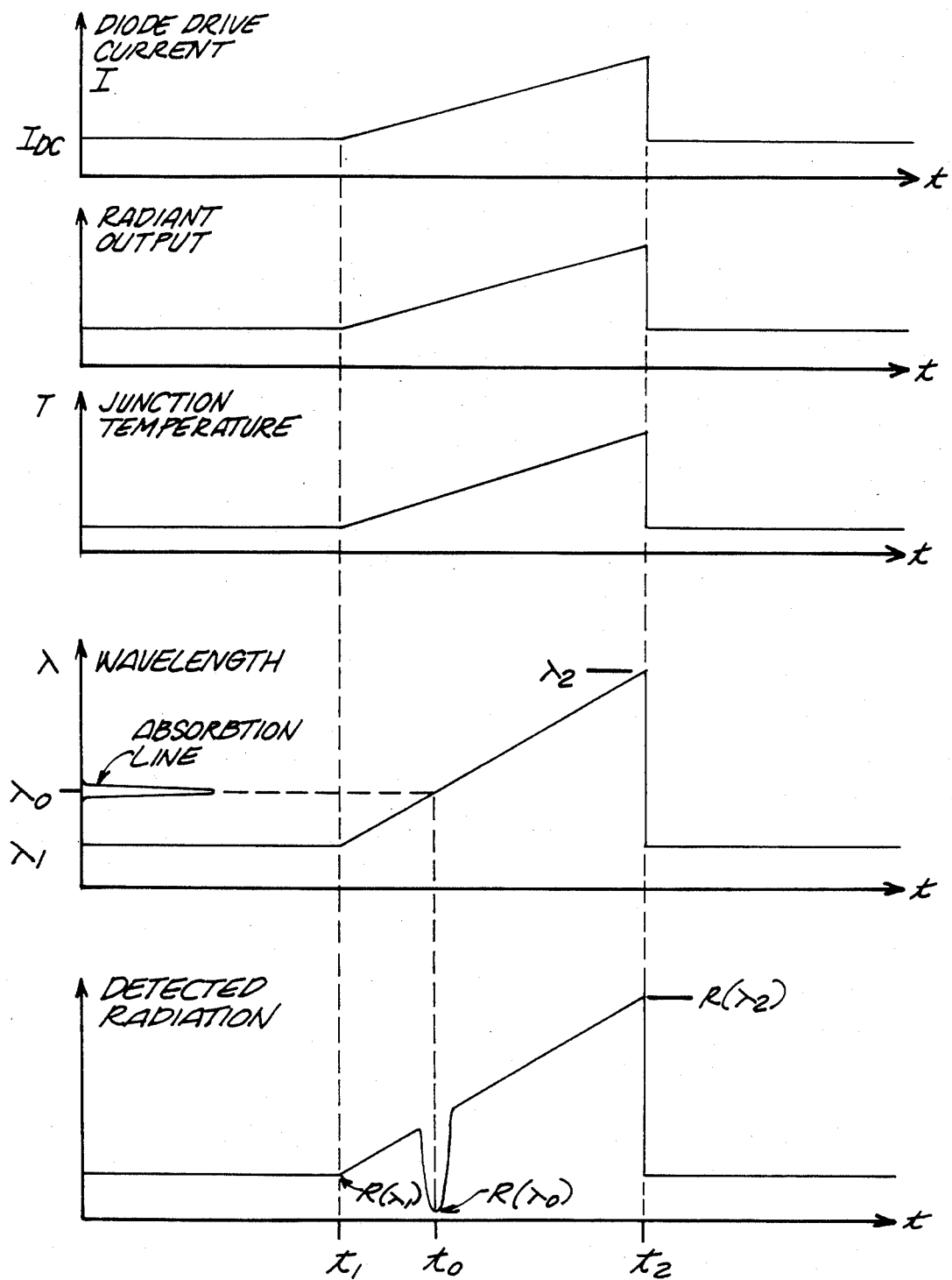
FIG. 5 is a related set of graphs showing how the diode drive current, radiant output, junction temperature, wavelength, and detected radiation vary with time in a linear type of scanning used in a preferred embodiment of the invention.

FIG. 5 is a set of related graphs showing a linear scanning method used in a preferred embodiment of the present invention. All of the graphs of FIG. 5 are with respect to time. In the scanning technique of FIG. 5, an initial diode drive current $I_{dc}$ maintains the radiant output and the junction temperature constant initially. The initial junction temperature maintains the laser output at the wavelength $\lambda_1$. Thereafter, at time $t_1$, the diode drive current is increased in a linear fashion. This has the effect of raising the radiant output in a linear fashion, and because of the small mass of the laser diode junction, its temperature also increases linearly following almost instantaneously the diode drive current.

The linear increase in the junction temperature results in a linear scanning of the wavelength from the initial wavelength $\lambda_1$ to a final wavelength $\lambda_2$. During this scan, the wavelength necessarily passes through the absorption line located at wavelength $\lambda_0$. The presence of this absorption line is manifested by a dip in the detected radiation occurring at the time $t_0$.

If there were no absorption line, the detected radiation would increase linearly, and the magnitude of the absorption is directly related to the difference between the radiation detected at the absorption line, $R(\lambda_0)$, and the radiation that would have been detected if there were no absorption.

It is immaterial that the radiant output is increasing during the scan, because the absorption is determined by comparing the detected radiation at time $t_0$ with the radiation that would have been detected at exactly the same time in the absence of absorption.

In connection with FIG. 5, it may be noted that the dip in the detected radiation could be detected by substracting the actual detected radiation signal shown in the bottom graph of FIG. 5 from a synthesized triangular waveform generated from the profile of the diode drive current.

It should also be noted from FIG. 5 that the scanned wavelength interval from $\lambda_1$ to $\lambda_2$ is not centered on the absorption line at $\lambda_0$, and this is manifested from the difference between $t_2-t_0$ and $t_0-t_1$. If the two differences were equal, the scanning interval would be centered on the absorption line at $\lambda_0$.

Figure 6:
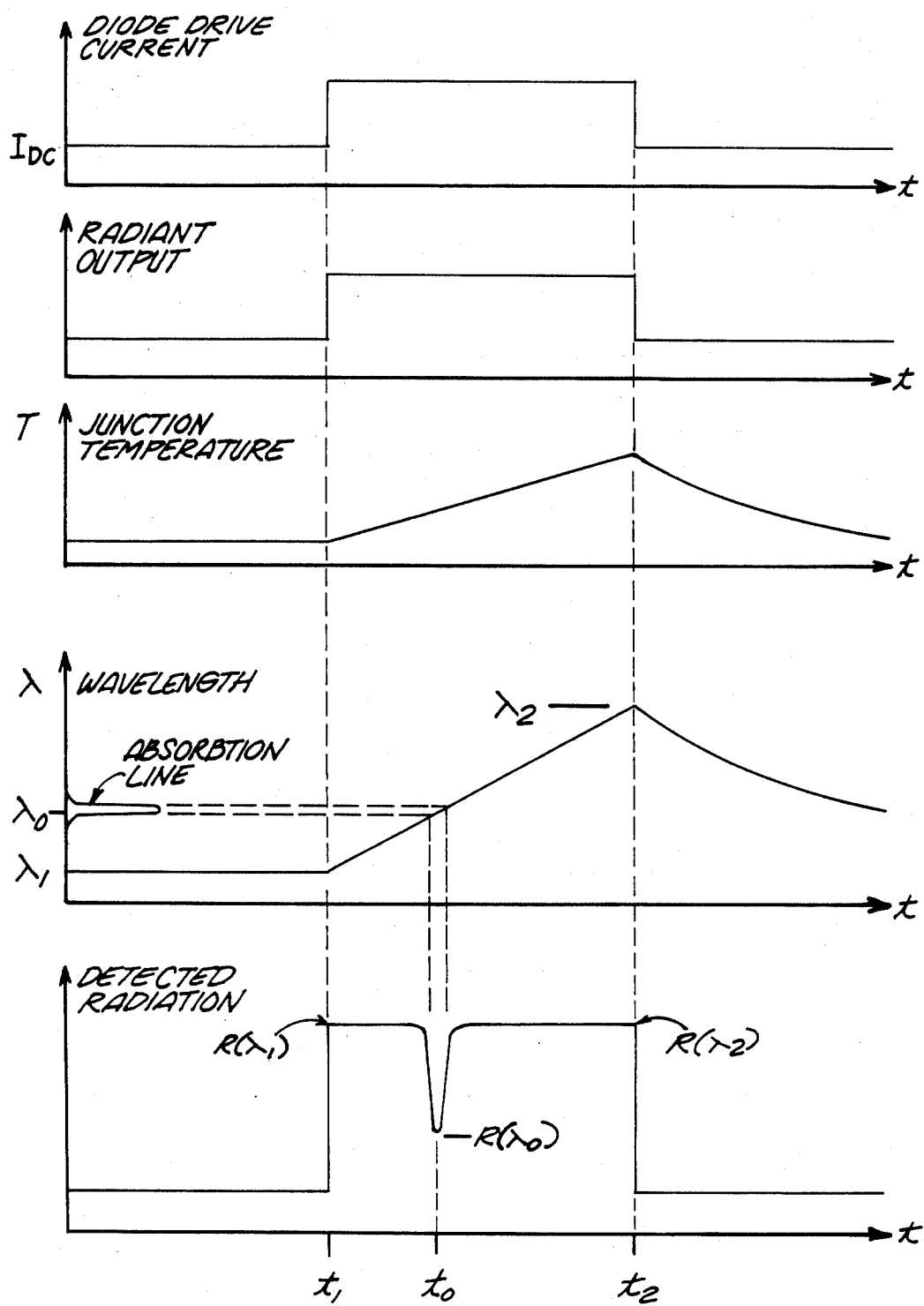
FIG. 6 is a set of related graphs showing how diode drive current, radiant output, junction temperature, wavelength, and detected radiation vary with respect to time in an alternative form of linear scanning used in a preferred embodiment of the invention.

FIG. 6 shows an alternative scanning technique that can be used when the laser junction has appreciable mass, and therefore the junction temperature does not instantaneously follow the profile of the diode drive current. In the related graphs of FIG. 6, the scan is initiated by applying a square pulse to the diode drive current. The radiant output is assumed to follow the current instantaneously. However, the junction temperature is assumed to increase linearly during the duration of the drive current pulse.

This linear increase in the junction temperature results in a linear scanning of the wavelength. As shown in the bottom graph, the detected radiation follows the diode radiant output except for the dip at time $t_0$ caused by the absorption line.

As in the case of FIG. 5, the absorption is determined by comparing the actual detected radiation $R(\lambda_0)$ at the time $t_0$ with the radiation that would have been detected if there had been no absorption.

Whether FIG. 5 or FIG. 6 is the closest approximation to the thermal behavior of the junction temperature depends on the many factors including the time interval $t_2-t_1$. However, between them, the two scanning schemes encompass all realistic possibilities.

Figure 7:
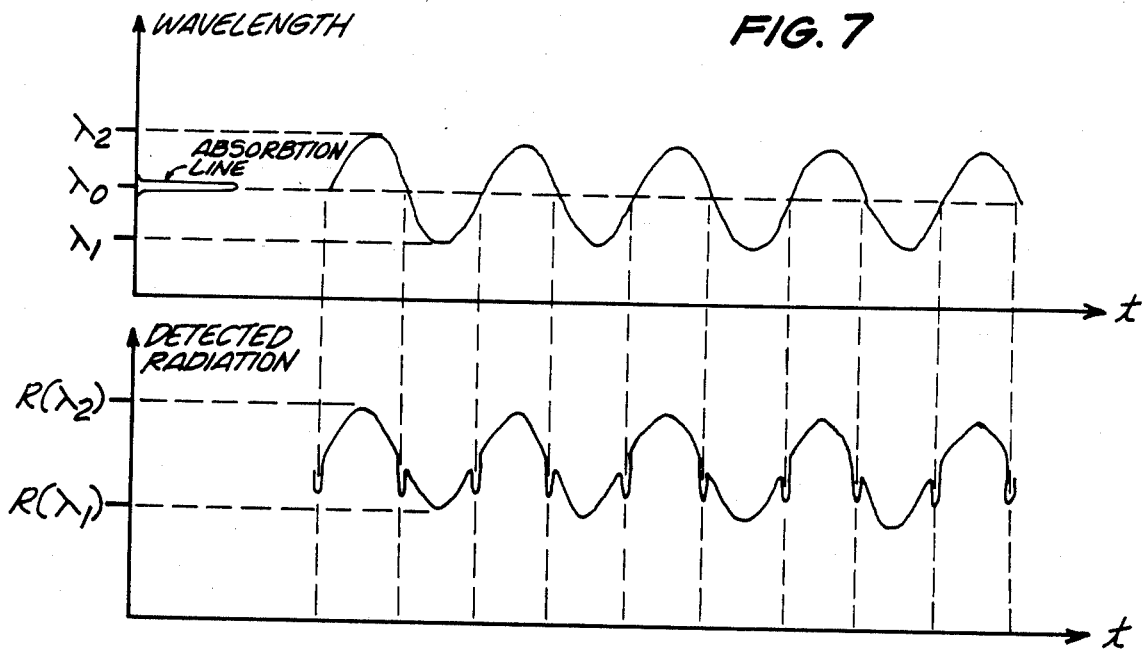
FIG. 7 is a related pair of graphs showing wavelength and detected radiation as a function of time for a sinusoidal type of scanning used in a preferred embodiment of the invention when the absorption line is centered within the scanned interval.

In addition to the linear diode drive current of FIG. 5 and the pulsed diode drive current of FIG. 6, it is also possible to modulate the drive current with a sinusoidal component. This approach is used in FIGS. 7 and 8 wherein it is assumed that the junction temperature follows the sinusoidal drive current instantaneously. FIG. 7 shows the wavelength and the detected radiation as functions of time, in a manner comparable to the lower two graphs in FIG. 5. Several cycles are shown in FIG. 7. In FIG. 7, the scan interval from $\lambda_1$ to $\lambda_2$ is centered about the absorption line at $\lambda_0$. In contrast, in FIG. 8 the scan interval is not centered on the wavelength $\lambda_0$.

Figure 8:
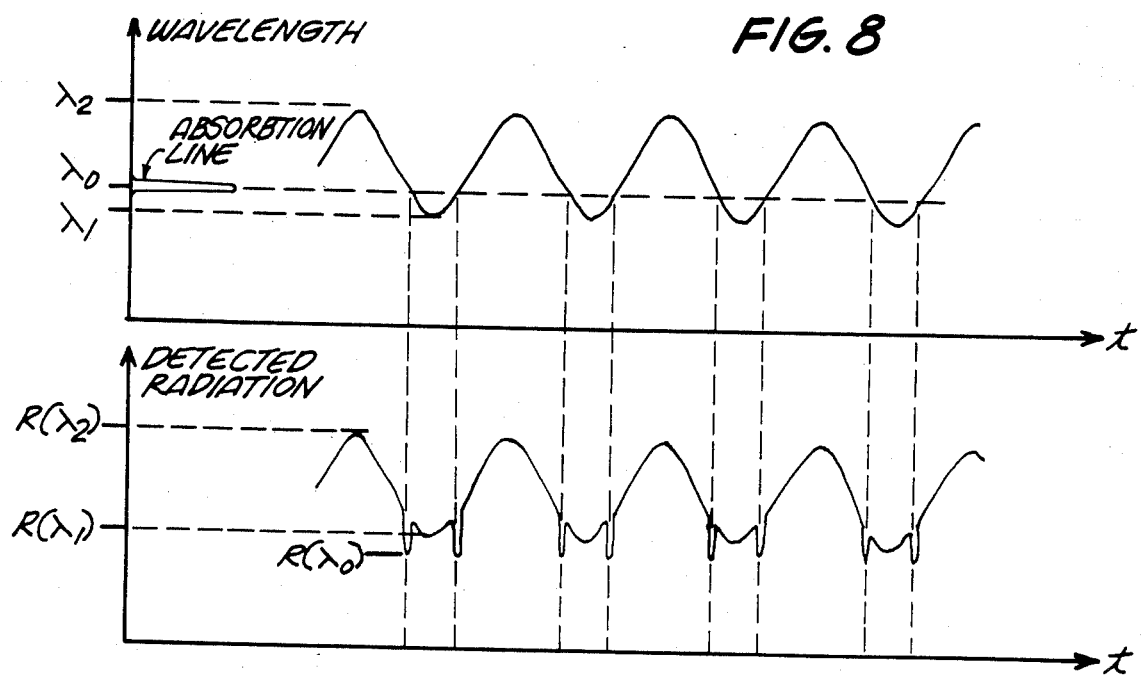
FIG. 8 is a pair of related graphs showing wavelength and detected radiation similar to FIG. 7, but for the case when the absorption line is not centered within the interval scanned.

Comparing the detected radiation graphs of FIGS. 7 and 8, it appears that when the absorption line is centered within the scanning interval, the absorption dips are equally spaced as in FIG. 7, but when the scanning interval is not centered on the absorption line, as in FIG. 8, the absorption dips have a different and unique spacing. In FIG. 7, the absorption dips occur with a single frequency equal to twice the frequency of modulation, while in contrast, in FIG. 8 two sidebands are present in addition to the center frequency.

In the sinusoidal scanning technique of FIGS. 7 and 8, it would be easy to detect the absorption dips by substracting the detected radiation signal from a sine wave of the same amplitude and frequency derived from the drive current.

The scanning techniques shown in FIGS. 5-8 are intended to be exemplary and are not the only techniques that could be used. For example, the sinusoidal modulation of FIGS. 7 and 8 could be replaced by the sawtooth pattern it approximates.

Figure 9:
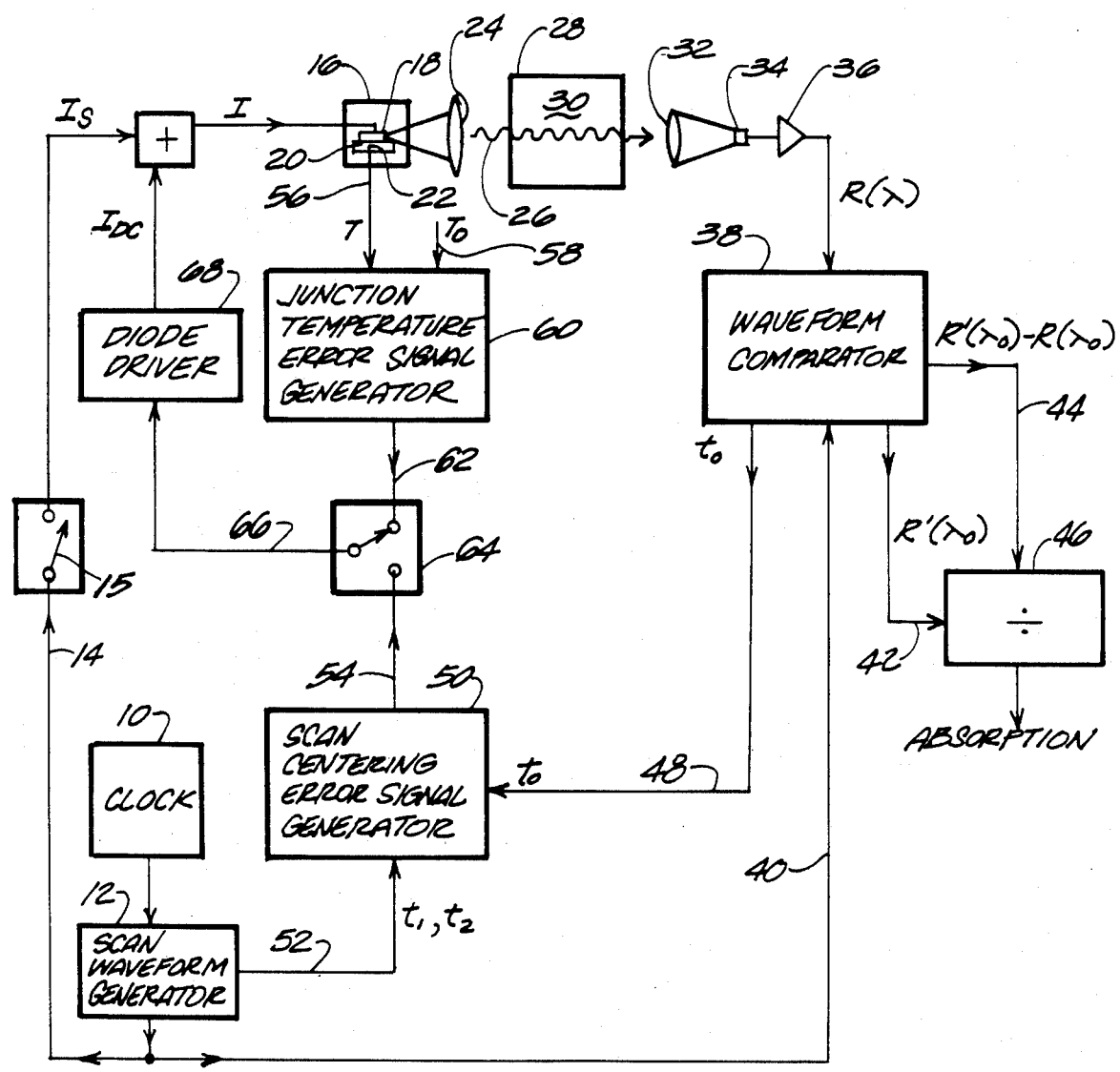
FIG. 9 is a block diagram showing the electronic system used with a preferred embodiment of the present invention.

FIG. 9 shows a block diagram of the circuits used in a preferred embodiment of the absorption measuring apparatus. Timing signals from the clock 10 are applied to the scan waveform generator 12 which generates the desired diode current modulation on the line 14. This alternating component is added to a dc component of the diode drive current and the sum is then applied to the diode laser 16. The scanning may be stopped by opening the switch 15. The passage of the current through the junction 18 gives rise to radiation which is collected by the lens 24 and formed into a beam 26. The beam 26 is passed through a sample 30 of oxygen, which may be contained in a sample cell 28. The radiation that has passed through the sample 30 is collected by the lens 32 and concentrated upon the detector cell 34. The detector cell 34 generates an electrical signal representative of the intensity of the radiation upon it, and that signal is amplified by the preamplifier 36 and thereafter denoted as $R(\lambda)$.

As described in connection with FIGS. 5-8, the waveform of the signal $R(\lambda)$ bears a great similarity to the waveform of the diode drive current and differs from it only in the dips caused by absorption. Thus, a waveform identical to $R(\lambda)$ can readily be synthesized from the signal generated by the scan waveform generator 12, which signal is applied to the waveform comparator 38 on the line 40. The waveform comparator 38 substracts the measured signal $R(\lambda)$ from the synthesized waveform $R'(\lambda)$ to obtain a difference signal $R'(\lambda)-R(\lambda)$ that consists only of the absorption dips inverted. The waveform comparator 38 detects the occurrence of these dips, and their occurrence within each scan determines $t_0$, the instant at which the wavelength is scanned across the absorption line. Upon detection of an absorotion dip, the difference signal, now denoted as $R'(\lambda_0)-R(\lambda_0)$ and the synthesized value, now denoted as $R'(\lambda_0)$ are gated into a sample and hold circuit from which they are made available via the lines 42 and 44 to the dividing circuit 46. The quotient of the difference divided by the synthesized value is the fractional absorption that was to be measured.

The time $t_0$ determined by the waveform comparator 38 is applied via the line 48 to the scan centering error signal generator 50. The times $t_1$ and $t_2$ available from the scan waveform generator 12 are also applied via the line 52 to the scan centering error signal generator 50, which generates a scan centering error signal on the line 54. In a preferred embodiment, the scan centering error signal is proportional to $(t_0-t_1)-(t_2-t_0)$. Thus, if the absorption line is encountered too early in the scan, as in FIG. 5, the error signal will be negative so as to reduce the dc component of the diode drive current, thereby shifting $\lambda_1$ and $\lambda_2$ towards shorter wavelengths. The effect of this feedback control system is to shift the scan interval in such a way that the absorption line remains centered within the interval.

A thermocouple 22 may be bonded to the heat sink 20 of the diode to provide a measurement of the temperature T of the junction 18 on the line 56. The desired junction temperature corresponding to a particular absorption line is input on the line 58 to the junction temperature error signal generator 60, which supplies the difference $T_0-T$ on the line 62 as the junction temperature error signal. The use of this junction temperature feedback is especially helpful in locating initially the desired line on which to operate. Once the line has been located, the scan centering feedback system should prove effective in keeping the apparatus locked to the proper line. The switch 64 permits either feedback system to be employed, as desired. Whichever error signal is used, is applied on the line 66 to the diode driver 68 which generates the dc component of the laser drive current.

Figure 10:
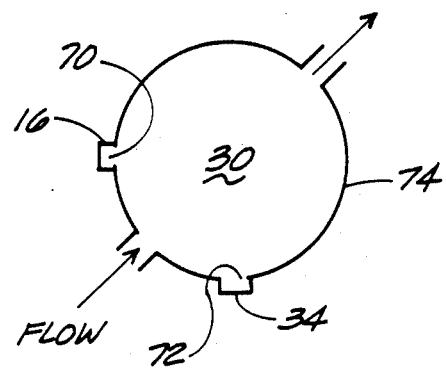
FIG. 10 is a diagram illustrating the use of an integrating sphere.

In the event the degree of absorption is inadequate to produce a measureable result, the optical path between the lens 24 and the lens 32 through the sample 30 can be extended by use of a cavity that provides for multiple reflection of the radiation. For example, the laser diode 16 and the detector 34 may be placed at the ports 70, 72 of an integrating sphere 74 as shown in FIG. 10. In the example shown, the entire interior of the integrating sphere serves as an airway or duct through which the sample may flow.

Certain other aspects of the invention will now be discussed, particularly as they relate to the second preferred embodiment shown in the block diagram of FIG. 14.

Figure 11:
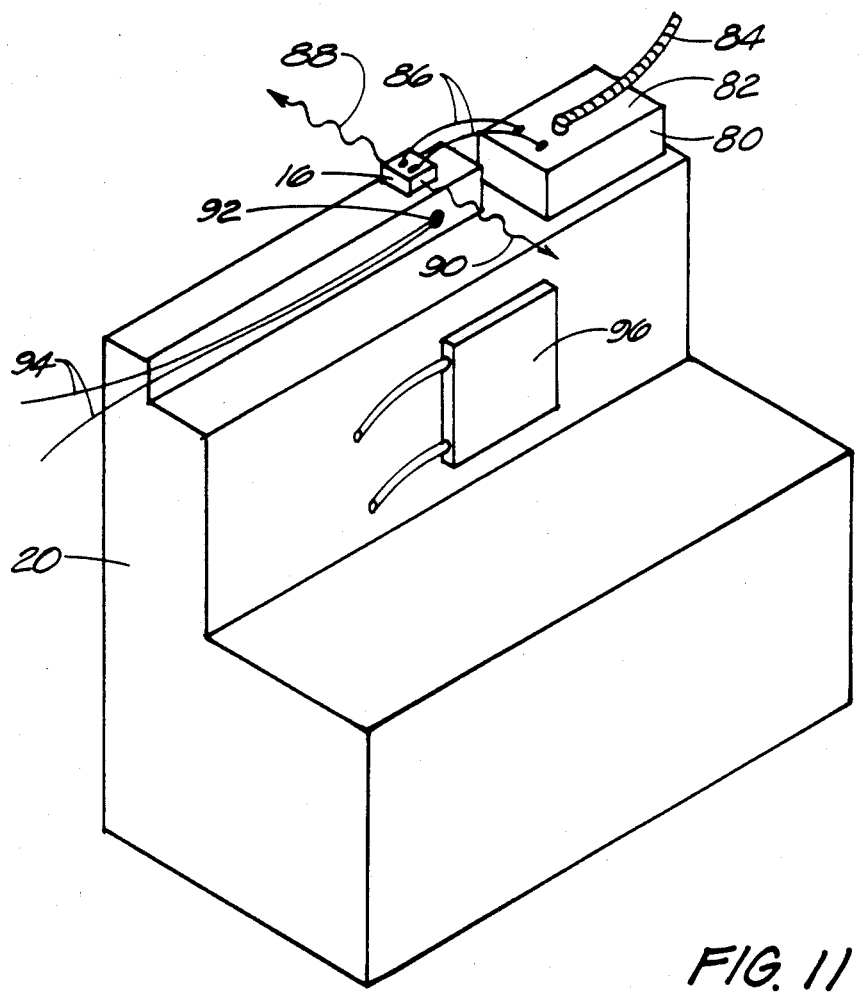
FIG. 11 is a perspective view showing a laser diode mounted on a heat sink.

FIG. 11 shows a greatly magnified view of the diode laser 16 and how it is mounted on the heat sink 20. This configuration is used in the second preferred embodiment that will now be described in connection with FIGS. 11-14.

In FIG. 11, the diode laser 16 is of the type that simultaneously emits radiation of exactly the same wavelength in two opposite directions. A first beam 88 of radiation is emitted in a first direction, and a second beam 90 of radiation is emitted in a second direction opposite the first direction. A negative lead 84 is bonded to a conductive surface 82 that is isolated from the heat sink 20 by a ceramic standoff 80. Jumper wires 86 conduct the current to the diode 16. The diode is in electrical and thermal contact with the heat sink 20, to which the positive lead is connected. A thermistor 92 is mounted in good thermal contact with the heat sink 20. Electrical connection to the thermistor 92 is made through the lead wires 94. In a variation of this embodiment, the thermistor 92 is replaced by a thermocouple. An electric heater 96 is mounted in thermal contact with the heat sink 20 for selectively providing heat to the heat sink for reasons that will presently be seen.

Figure 12:
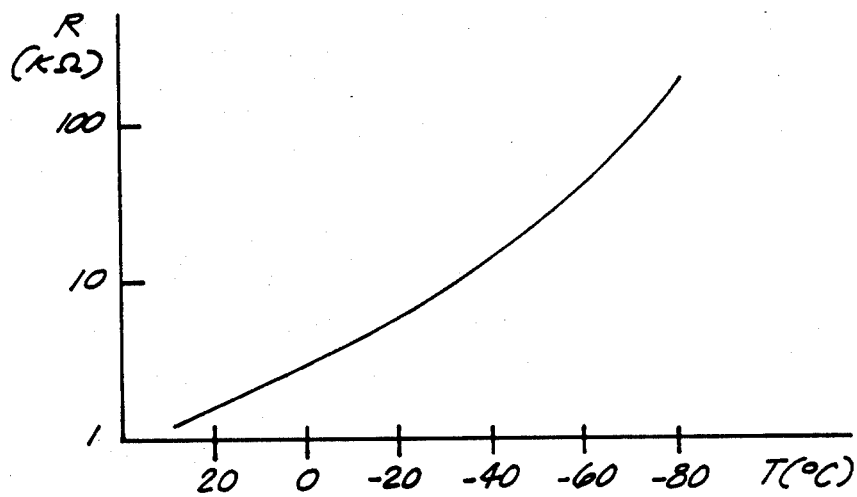
FIG. 12 is a graph showing the resistance of a thermistor as a function of temperature.

FIG. 12 is a graph showing the relationship between the resistance of a typical thermistor and the temperature of the thermistor. Clearly, if the resistance of the thermistor is known, then the temperature of the thermistor may be determined from this graph. Because of the high thermal conductivity of the heat sink 20, the temperature sensed by the thermistor 92 is approximately equal to the temperature of the junction of the laser diode 16.

Figure 13:
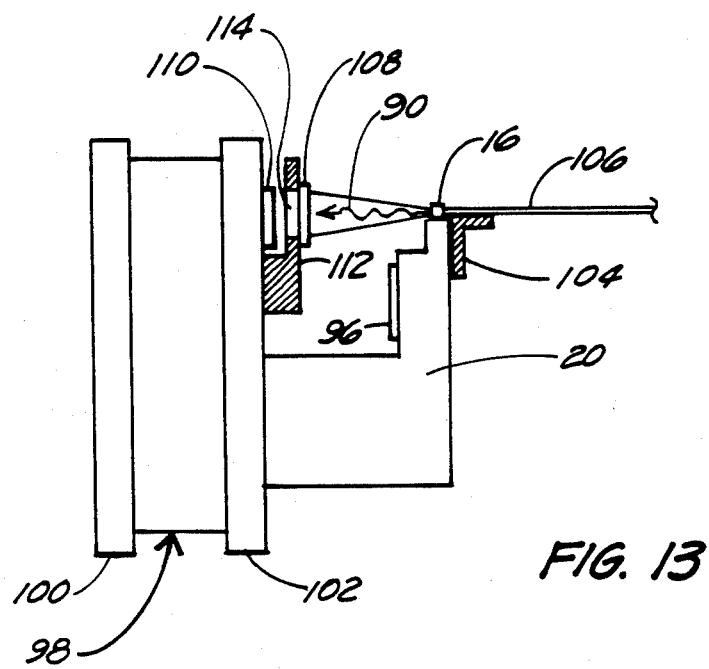
FIG. 13 is a diagram, partly in cross section showing the laser and heat sink of FIG. 11 mounted on a thermoelectric cooler; and, FIG. 14 is a block diagram showing the electronic system used with a second preferred embodiment of the present invention.

FIG. 13 shows the apparatus of FIG. 11 mounted on a thermoelectric cooler 98, which includes a hot junction 100 and a cold junction 102. The heat sink 20 is maintained in good thermal contact with the cold junction 102, so as to permit the heat generated by the diode laser 16 and the heater 96 to be transferred efficiently from the heat sink 20. A first bracket 104 supports an optical fiber 106 that is used for conducting the radiation 88 that is emitted in a first direction from the laser diode 16 to the sample under test. The radiation 90 emitted in a second direction first passes through a filter 108 and then falls on a detector 110. A second bracket 112 supports the filter 108 and includes an aperture 114 to pass the radiation 90. This arrangement permits the filter 108 and the detector 110 to be cooled to approximately the same temperature as the heat sink 20.

In the first preferred embodiment shown in FIG. 9, control of the temperature of the junction 18 of the diode laser 16 was achieved by altering the current flowing through the diode. The apparatus shown in FIGS. 11-13 makes possible a second means of controlling the temperature of the junction, namely by adding or removing heat from the junction via the heat sink 20 through the use of a thermoelectric cooler 98 or a heater 96 as the situation may require.

Because of the thermal inertia of the heat sink 20, the temperature of the junction 18 responds more quickly to variations in the current through the diode laser 16, and responds less quickly to the introduction of heat through the heater 96 or the removal of heat through the thermoelectric cooler 98. Accordingly, in the preferred embodiment, the relatively rapid scanning of the wavelength is brought about by altering the diode current in a systematic manner, while the slower variations in the wavelength are handled by applying heat or removing heat from the heat sink.

It is conceivable that in an extreme case the required dc component of the diode drive current might approach the maximum current the diode can tolerate. In this case, the advantage of being able to add and remove heat from the heat sink becomes especially clear. In the second preferred embodiment shown in FIG. 14, the scan centering function is shared by both the diode drive current and by the adding or removing of heat from the heat sink.

Because the diode laser 16 is itself a heater, there may be applications of the apparatus in which the heater 96 can be omitted. However, this possibility depends on how rapidly the diode laser can warm the heat sink. In turn, this depends on the dimensions of the heat sink and on the power level at which the diode laser is operated. In some applications, the diode laser may not be able to warm the heat sink fast enough to provide a desirably short response time. In such a case, the heater 96 permits a much more rapid response. Also, if the apparatus were to be operated in an extremely cold environment, the heater 96 could provide the additional heating capacity required to maintain a given temperature or to increase the temperature, considering that there is a maximum diode drive current that cannot be exceeded.

Because there is a maximum diode drive current which must not be exceeded because of the risk of destroying the diode, and because in some applications it may be desirable to operate the diode laser at a relatively high current to produce a relatively large radiation output, it would appear to be difficult to switch from one absorption line to another. The use of the thermoelectric cooler 98 and the heater 96 are especially valuable in such situations since they permit the diode temperature to be altered through a wide range without varying the diode drive current. As a result, using the embodiment of FIG. 14 as contrasted with the embodiment of FIG. 9 permits several predetermined absorption lines to be examined, provided they are not too widely separated in wavelength.

Figure 14:
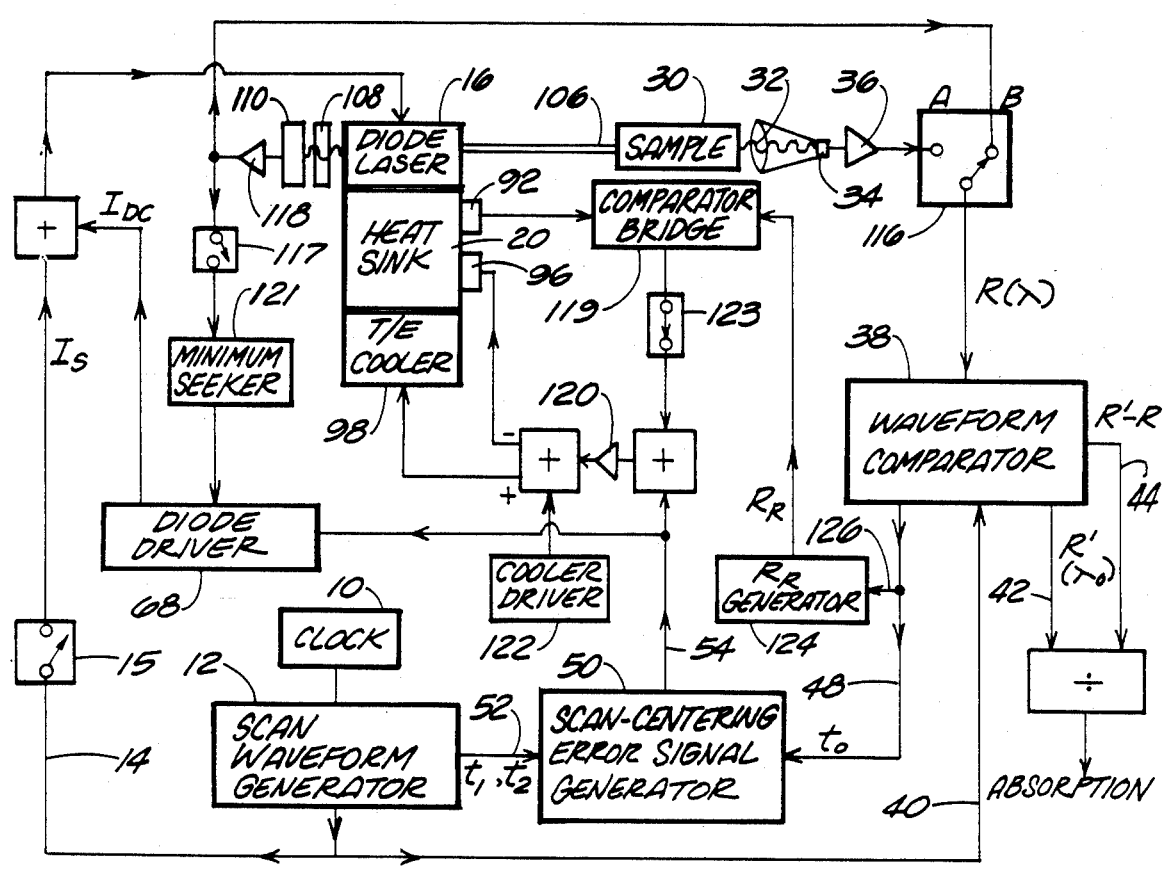

Referring now to FIG. 14, the diode laser 16 emits radiation 88 in a first direction which is conducted by the optical fiber 106 to the sample 30. Whatever radiation penetrates the sample 30 is concentrated by the lens 32 onto the detector 34 which produces an electrical signal related to the intensity of the radiation that has passed through the sample 30. The electrical signal is amplified by the preamplifier 36 and applied via the switch 116 to the waveform comparator 38. The signal is then processed in the manner described above in connection with FIG. 9.

The diode laser also emits radiation 90 in a second direction opposite the first direction. This beam of radiation passes through the filter 108, and falls on the detector 110. The detector 110 produces an electrical output that is related to the intensity of the radiation, and that output is amplified by the amplifier 118. The resulting amplified signal is applied to the waveform comparator 38 through the switch 116.

In a first and preferred variation of this embodiment, the filter 108 is a narrow band rejection filter which strongly absorbs radiation in a narrow band centered on a chosen wavelength, but is substantially transparent to radiation of other wavelengths. Thus, the filter 108 is indistinguishable from a sample that has a strong absorption line at the chosen wavelength. The chosen wavelength ordinarily would equal either $\lambda_o$ or $\lambda_1$ of FIGS. 5-8.

In another variation of the second preferred embodiment of FIG. 14, the filter 108 is a narrow band pass filter that passes radiation in a narrow wavelength band centered on a chosen wavelength but which is substantially opaque to radiation outside that band. In this case, the dips in the detected radiation shown in FIGS. 5-8 will be of opposite polarity and will appear as peaks. The waveform comparator 38 will detect peaks instead of dips, and the polarity of the detected signal can easily be reversed.

The normal scanning mode of the instrument of FIG. 14 will now be described in detail; that mode is used for making the absorption measurement. Thereafter, the initializing mode will be described; it is used during start-up to give positive assurance that the instrument operates at the chosen wavelength.

If the scan is not centered on $\lambda_o$, as indicated by the scan centering error signal generator 50, the error signal on the line 54 is applied both to the diode driver 68 and to the cooling system servo. In the embodiment of FIG. 14, the diode driver has a response curve that saturates at larger values of the error signal so as to avoid increasing the diode drive current beyond a safe level. If the error signal continues to increase from that point, then whatever additional correction is to be applied, will be applied by the cooling system servo, rather than by further increases in the diode drive current.

This combined error signal is then amplified by the amplifier 120, and the amplified signal is combined with a steady state signal produced by the cooler driver 122. This latter signal tends to cancel the steady influx of heat into the heat sink from the diode laser. The combined signal is then applied either to the heater 96 or to the cooler 98 depending upon the polarity of the signal. In either case, the temperature of the heat sink will be altered, and along with it the diode laser temperature will be altered, in the desired direction.

When the instrument is first turned on, it is most likely that the heat sink 20 will be at ambient temperature rather than at the temperature $T_c$ that corresponds to laser operation at some chosen wavelength $\lambda_c$. Initially, the switch 15 is open to disable the scanning action, and the scan centering error signal on the line 54 is zero. The diode driver 68 applies a constant current to the diode laser 16.

In accordance with the second preferred embodiment of the present invention of FIG. 14 there is provided a coarse and a fine wavelength control system. The coarse system makes use of the heater 96 and the thermoelectric cooler 98 to add or remove heat from the heat sink 20, thereby altering the temperature of the heat sink, thereby indirectly altering the temperature of the diode laser 16. The temperature of the heat sink is sensed by the thermistor 92, the resistance of which varies with the temperature as discussed in connection with FIG. 12. The instantaneous resistance R is compared in the comparator bridge circuit 119 with a reference resistance $R_R$ provided by the $R_R$ generator 124. A current representing the difference in the resistances is amplified by the amplifier 120 and combined with the cooler drive current generated by the cooler driver 122. The resulting current is then applied to the thermoelectric cooler 98 or to the heater 96, depending on the polarity of the difference. Through the use of this coarse control system, the diode laser 16 is brought to approximately the temperature $T_c$, which (ideally) brings the wavelength of the emitted radiation to within a scan interval of the chosen wavelength $\lambda_c$. At this point the switch 123 is opened and the switch 117 is closed to initiate operation of the fine control system.

The $R_R$ generator 124 initially provides the input reference resistance $R_R$ to the comparator bridge 119. However, in an optional variation of this embodiment, if no absorption line is found in the scanning interval, then the $R_R$ generator 124 is pre-programmed to substitute another resistance value for $R_R$. This has the effect of displacing the scanning interval, thereby allowing the system to execute a pre-programmed search pattern. It is believed that the need for this feature would arise very seldom, and accordingly, the feature is regarded as optional.

The operation of the fine control system is controlled by the minimum seeker 121. It calls for more or less current to be applied by the diode driver 68 to the diode laser 16. The wavelength responds to these changes in the current. Since it is known that a minimum is sought, corresponding to the rejection band of the filter 108, the minimum seeker 121 evaluates each stepwise change in the current. If a change has resulted in less detected radiation, the step must have been in the right direction, and so the next step is taken in the same direction. A step that results in increased detected radiation is a step in the wrong direction, and so it is followed by two steps in the opposite direction. Circuits of this type are known in the art and need not be described in detail. The steps may be very small, and the time between successive steps can be quite short. Through the operation of the minimum seeker circuit 121, the wavelength of the emitted radiation can be brought extremely close to the chosen wavelength $\lambda_c$. Thereafter, the switch 117 can be opened and the switch 15 closed to initiate the wavelength scanning action used in the absorption measurement process, as described above in connection with FIG. 9.

In an alternative variation of this wavelength determining technique, if the coarse control system is capable of rendering the wavelength of the emitted radiation equal to the chosen wavelength $\lambda_c$ with an accuracy of better than one scan interval, it is possible to initiate scanning at the conclusion of the coarse adjustment.

Thus, the second alternative embodiment shown in FIG. 14 provides for measuring the temperature of the diode laser by means of the thermistor 92 to insure that the temperature is such as to permit the wavelength of the emitted radiation to approximate a chosen wavelength. The system further provides a filter 108 that positively identifies the desired absorption line when the chosen filter wavelength equals $\lambda_o$.

The laser spectral scanning technique described above can be applied to any particular line when a multi-mode laser is used as a source.

The advantages of the absorption measurement technique described above are many-fold. First and foremost, this technique affords an extremely stable mode of sampling due to the ratioing aspect inherent in the technique. The measured ratio is not only independent of the laser output power level, but it is also immune to any drifts of the detector and any changes in the optical system such as windows, etc., and changes caused by environmental effects.

Secondly, the technique of the present invention is very specific and almost completely free from any interference effects even in the presence of other gases. This is because of the fact that no other gases are known to have spectral signatures in the oxygen "A" region.

Thirdly, the technique is linear due to the spectral matching of the source and the absorption lines and also due to the weakness of the oxygen "A" system.

The foregoing detailed description is illustrative of several embodiments of the invention, and it is to be understood that additional embodiments thereof will be obvious to those skilled in the art. The embodiments described herein together with those additional embodiments are considered to be within the scope of the invention.

What is claimed is:

1. Apparatus for use in an instrument that measures the absorption of a sample by passing radiation through the sample, the sample having more than one absorption line including an absorption line at wavelength $\lambda_o$, said apparatus serving to positively identify the absorption line being measured as the absorption line at wavelength $\lambda_o$, said apparatus comprising:

source means including a diode laser responsive to an applied electric current to produce radiation and emitting a part of that radiation in a first direction toward the sample, and emitting another part of that radiation in a second direction;

a first detector positioned to receive radiation that was emitted in the first direction after it has passed through the sample, and generating a first electrical signal related to the intensity of the radiation received by said first detector;

a filter positioned to intercept the radiation emitted in said direction and having a narrow rejection band centered at wavelength $\lambda_o$ and substantially transmitting radiation of wavelengths outside the narrow rejection bank;

a second detector positioned to receive radiation that has passed through said filter, and generating a second electrical signal related to the intensity of the radiation received by said second detector;

first means connected to said diode laser for scanning the wavelength of the radiation emitted through a wavelength interval in a continuous manner; and, second means, connected to said first means and to said second detector, and responsive to the second electrical signal generated by said second detector to determine at what instant in the scanning the wavelength of the radiation emitted by said diode laser equals $\lambda_o$.

2. The apparatus of claim 1 wherein said first means further comprise means for systematically varying the current applied to said diode laser, thereby scanning the wavelength of the emitted radiation in a systematic manner.

3. The apparatus of claim 1 wherein said first means further comprise means for systematically cooling and heating said diode laser, thereby scanning the wavelength of the emitted radiation in a systematic manner.

4. Apparatus for use in an instrument that measures the absorption of a sample by passing radiation through the sample, the sample having more than one absorption line including an aboorption line at wavelength $\lambda_o$, said apparatus serving to positively identify the absorption line being measured as the absorption line at wavelength $\lambda_o$, said apparatus comprising:

source means including a diode laser responsive to an applied electric current to produce radiation and emitting a part of that radiation in a first direction toward the sample, and emitting another part of that radiation in a second direction;

a first detector positioned to receive radiation that was emitted in the first direction after it has passed through the sample, and generating a first electrical signal related to the intensity of the radiation received by said first detector;

a filter positioned to intercept the radiation emitted in said second direction and having a narrow pass band centered at wavelength $\lambda_o$ and substantially opaque to radiation of wavelengths outside the narrow pass band;

a second detector positioned to receive radiation that has passed through said filter, and generating a second electrical signal related to the intensity of the radiation received by said second detector;

first means connected to said diode laser for scanning the wavelength of the radiation emitted through a wavelength interval in a continuous manner; and second means, connected to said first means and to said second detector, and responsive to the second electrical signal generated by said second detector to determine at what instant in the scanning the wavelength of the radiation emitted by said diode laser equals $\lambda_o$.

5. The apparatus of claim 4 wherein said first means further comprise means for systematically varying the current applied to said diode laser, thereby scanning the wavelength of the emitted radiation in a systematic manner.

6. The apparatus of claim 4 wherein said first means further comprise means for systematically cooling and heating said diode laser, thereby scanning the wavelength of the emitted radiation in a systematic manner.

7. Apparatus for controlling the wavelength of the radiation emitted by a diode laser that is mounted on a heat sink, to equal a particular wavelength $\lambda_c$ where the wavelength is a known function of the temperature of the junction of the diode laser, and $T_c$ is the temperature corresponding to $\lambda_c$ said apparatus comprising:

a coarse control system for comparing the temperature of the heat sink with $T_c$ and for applying heat to or removing heat from the heat sink as required to cause the temperature of the heat sink to approach $T_c$; and, a fine control system for altering the diode laser current in a systematic way to maximize the transmission of a sample of the radiation through a narrow band pass filter having its pass band centered at the wavelength $\lambda_c$.

8. Apparatus for controlling the wavelength of the radiation emitted by a diode laser that is mounted on a heat sink, to equal a particular wavelength $\lambda_c$ where the wavelength is a known function of the temperature of the junction of the diode laser, and $T_c$ is the temperature corresponding to $\lambda_c$ said apparatus comprising:

a coarse control system for comparing the temperature of the heat sink with $T_c$ and for applying heat to or removing heat from the heat sink as required to cause the temperature of the heat sink to approach $T_c$; and, a fine control system for altering the diode laser current in a systematic way to minimize the transmission of a sample of the radiation through a narrow band rejection filter having its rejection band centered at the wavelength $\lambda_c$.

* * * * *